United States Patent [19]

Wink et al.

[11] Patent Number: 5,089,521

[45] Date of Patent: Feb. 18, 1992

[54] 10-MEMBERED RING LACTONES, A PROCESS FOR THE PREPARATION THEREOF, AND THE USE THEREOF

[75] Inventors: Joachim Wink, Offenbach; Susanne Grabley, Königstein/Taunus; Gerhard Seibert, Darmstadt; Klaus Hütter, Bad Soden am Taunus; Axel Zeeck, Göttingen, all of Fed. Rep. of Germany

[73] Assignee: Hoechst Aktiengesellschaft, Frankfurt, Fed. Rep. of Germany

[21] Appl. No.: 563,682

[22] Filed: Aug. 3, 1990

Related U.S. Application Data

[63] Continuation of Ser. No. 322,461, Mar. 13, 1989, abandoned.

Foreign Application Priority Data

Mar. 15, 1988 [DE] Fed. Rep. of Germany ....... 3808492

[51] Int. Cl.⁵ .................. A61K 31/335; C07D 315/00
[52] U.S. Cl. .................. 514/450; 549/269; 549/270; 549/271
[58] Field of Search ........ 549/269, 270, 271; 511/450

[56] References Cited

PUBLICATIONS

Wakamatsu et al., "Naturally Occurring Ten-Membered Lactones: Total Synthesis of (±)-Diplodialide C, and (±)-Decan-9-olide," The Journal of Organic Chemistry, vol. 44, No. 12, pp. 2008-2012 (1979).

*Primary Examiner*—Richard L. Raymond
*Assistant Examiner*—Mark W. Russell
*Attorney, Agent, or Firm*—Finnegan, Henderson, Farabow, Garrett, and Dunner

[57] ABSTRACT

New 10-membered ring lactones, a process for the preparation thereof, and the use thereof.

It is possible with the aid of Penicillium strains to prepare new 10-membered ring lactones having a pharmacological action.

5 Claims, No Drawings

10-MEMBERED RING LACTONES, A PROCESS FOR THE PREPARATION THEREOF, AND THE USE THEREOF

This is a continuation of application Ser. No. 07/322,461, filed Mar. 13, 1989, now abandoned.

DESCRIPTION

New 10-membered ring lactones, a process for the preparation thereof, and the use thereof Antibiotics from Penicillium, such as, for example, penicillin, have been known for a long time.

It has been found that Penicillium strains are also able to synthesize substances with a quite different structure, namely 10-membered ring lactones These compounds have pharmacological and thus therapeutic activity and can be used advantageously as antibacterial agents, in particular.

Hence the invention relates to:
1. A compound of the general formula I

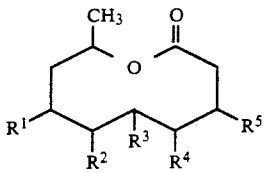

in which, independently of one another, $R^1$ and $R^4$ are hydrogen and hydroxyl, $R^2$ and $R^3$ are hydroxyl, $R^5$ is hydrogen, hydroxyl and oxogroup and $R^2$ and $R^3$, and $R^3$ and $R^4$, can each together form a double bond, and $R^1$ and $R^2$ can represent, together with the carrying carbon atoms, an oxirane ring.

2. A process for the preparation of the compound of the general formula I as claimed in claim 1, which comprises cultivating Penicillium sp. in a nutrient medium until the compound of the general formula I accumulates in the culture.

3. A use of the compound of the general formula I as an antibacterial agent.

The invention is described in detail hereinafter, especially in its preferred embodiments. The invention is also defined in the patent claims.

The invention is preferably carried out with Penicillium sp. DSM 4209 and DSM 4210. These strains were isolated from a sample of soil from Bryce Canyon, Utah, USA and deposited under the abovementioned numbers at the Deutsche Sammlung von Mikroorganismen (German Microorganism Collection) in compliance with the rules of the Budapest Treaty on August 13, 1987. Conidia and spores of the fungus have the following characteristics:
Conidia: monoverticilliata
Spore surface spiky
Spore colour: gray-green.

In a nutrient solution which contains a carbon source and a nitrogen source as well as the customary inorganic salts Penicillium spec., preferably DSM 4209 and DSM 4210, produces the compound of the general formula I. It is of course also possible to use in place of the strains DSM 4209 or 4210 the mutants and variants thereof as long as they synthesize this compound Such mutants can be generated in a manner known per se by physical means, for example irradiation, such as with ultraviolet radiation or X-rays, or chemical mutagens such as, for example, ethyl methanesulfonate (EMS), 2-hydroxy-4-methoxybenzophenone (MOB) or N-methyl-N'-nitro-N-nitrosoguanidine (MNNG).

Suitable and preferred carbon sources for the aerobic fermentation are assimilable carbohydrates and sugar alcohols such as glucose, lactose or D-mannitol, as well as carbohydrate-containing natural products such as malt extract. Suitable nitrogen-containing nutrients are amino acids, peptides and proteins as well as the degradation products thereof, such as peptones or tryptones, furthermore meat extracts, ground seeds, for example of corn, wheat, beans, soybeans or the cotton plant, distillation residues from the production of alcohol, meat meals or yeast extracts, but also ammonium salts and nitrates. Examples of other organic salts which the nutrient solution can contain are chlorides, carbonates, sulfates or phosphates of the alkali metals or alkaline earth metals, iron, zinc and manganese.

The formation of the compound of the formula I takes place especially well in a nutrient solution which contains about 0.2 to 5%, preferably 1 to 4%, malt extract, 0.02 to 0.5%, preferably 0.1 to 0.4%, yeast extract, 0.1 to 5%, preferably 0.5 to 2%, glucose and 0.005 to 0.2%, preferably 0.01 to 0.1%, ammonium salt, in each case based on the weight of the complete nutrient solution. Cultivation is carried out aerobically, that is to say, for example, submerged with shaking or stirring in shaken flasks or fermenters, where appropriate with introduction of air or oxygen. It can be carried out in a temperature range of about 18 to 35° C, preferably at about 25 to 30° C, in particular at 27 to 28° C. The pH range should be between 6 and 8, advantageously between 6.5 and 7.5. The microorganism is cultivated under these conditions for a period of, in general, 60 to 170 hours, preferably 100 to 150 hours.

The cultivation is advantageously carried out in several stages, i.e. one or more precultures are first prepared in a liquid nutrient medium and are then transferred into the actual production medium, the main culture, for example in the ratio 1:10 by volume. The preculture is obtained, for example, by transferring a sporulated mycelium into a nutrient solution and leaving it to grow for about 48 to 72 hours. The sporulated mycelium can be obtained by leaving the strain to grow for about 7 days on a solid or liquid nutrient medium, for example yeast-malt agar.

The progress of the fermentation can be monitored by means of the pH of the culture or of the mycelium volume, or by thin-layer chromatography or testing the biological activity. The compound of the general formula I is present both in the mycelium and in the culture filtrate.

The said compound is isolated from the culture medium by known methods, taking account of the chemical, physical and biological properties of the products. In order to assay the antibiotic concentration in the culture medium or in the individual steps in the isolation it is possible to use thin-layer chromatography, for example on silica gel with chloroform/methanol as mobile phase, the amount of antibacterial substance formed expediently being compared with a calibration solution.

To isolate the compound, the culture broth and mycelium are first extracted with organic solvents such as, for example, chloroform, ethyl acetate etc. in order to remove non-polar impurities. Extraction with a polar solvent, for example lower alkanols or mixtures of chloroform and/or ethyl acetate with a lower alkanol, is then carried out.

Isolation of the pure product is preferably carried out on suitable media such as, for example, silica gel, alumina or ion exchangers, by subsequent elution with organic polar solvents or solvent mixtures, such as, for example, alkyl acetates, mixtures of alkyl acetates and a lower alkanol, where appropriate with water, or with a salt gradient suitable for ion exchangers, such as, for example, sodium chloride or tris(hydroxymethyl)aminomethane-HCl (tris buffer) and collection of the fractions having antibiotic activity.

The compounds are stable in the solid state and in solutions in the pH range 2 to 8, in particular 3 to 7, and thus can be incorporated in customary pharmaceutical preparations.

The invention is described in further detail in the examples which follow. Unless indicated otherwise, percentage data relate to weight.

EXAMPLES 1. (a) preparation of a suspension of spores of the producer strain:

100 ml of nutrient solution (2 g of yeast extract, 20 g of malt extract, 10 g of glucose, 0.5 g of $(NH_4)_2HPO_4$, 1 l of tap water, pH before sterilization 7.3) in a 500 ml Erlenmeyer flask are inoculated with the strain DSM 4209 or DSM 4210 and incubated in a rotating shaker at 120 rpm and 25° C for 72 hours. Then 20 ml of culture liquid are uniformly distributed in a 500 ml Erlenmeyer flask containing the nutrient medium of the abovementioned composition, to which 20 g of agar/1 have been added for solidification, and decanted. The cultures are incubated at 25° C for 10 to 14 days. The spores which have been produced after this time in a flask are rinsed out with 500 ml of deionized water containing 1 drop of a commercially available non-ionic surfactant (Triton × 100, from Serva) and immediately used further or stored at −22° C.

(b) preparation of a culture or preculture of the producer strain in Erlenmeyer flasks.

A 500 ml Erlenmeyer flask containing 100 ml of the nutrient solution described under a) is inoculated with a culture grown in a slant tube or with 0.2 ml of spore suspension and incubated in a shaker at 120 rpm and 25° C. The maximal production of the compound of the formula I is reached after about 120 hours. A 48-hour old submerged culture (5%) from the same nutrient solution suffices to inoculate 10 and 100 l fermenters.

2. Preparation of the compound of the general formula I

A 10 l fermenter is operated under the following conditions:
Nutrient medium: 20 g/l malt extract, 2 g/l yeast extract, 10 g/l glucose, 0.5 g/l $(NH_4)_2HPO_4$, pH 7.2.
Incubation time: 150 hours
Incubation temperature: 25° C.
Stirrer speed: 250 rpm
Aeration: 4 l of air/min.

Foam development can be suppressed by repeated addition of a few drops of ethanolic polyol solution. The production maximum is reached after about 150 hours. The yields are about 100 mg/l.

3. Isolation of the compound of the general formula I

After the fermentation of DSM 4209 or DSM 4210 the culture broth is filtered with the addition of 2% Celite as filtration aid. The procedure is shown in the following diagrams:

Working up/isolation

Diagram 1: Culture supernatant

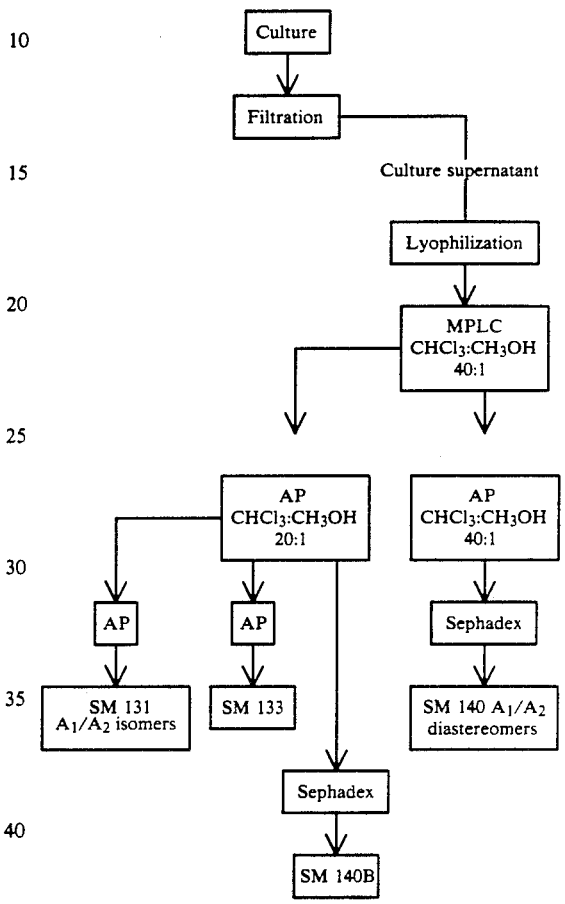

Working up/isolation

Diagram 2: mycelium

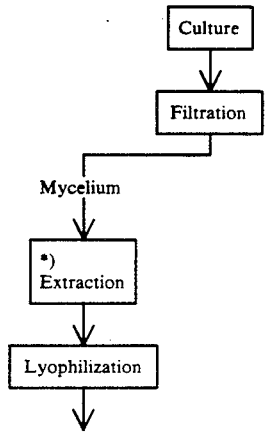

-continued

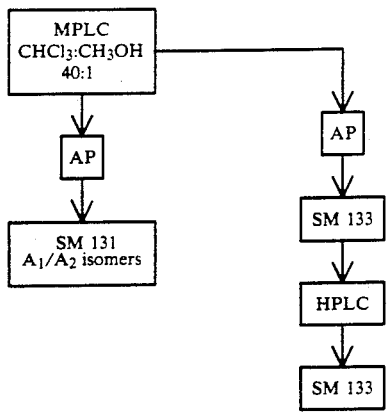

Abbreviations:
MPLC: Medium pressure liquid chromatography
AP: Atmospheric pressure column chromatography
*) Where appropraiate after disruption with homogenizers 1. Characteristic of the compounds SM 131

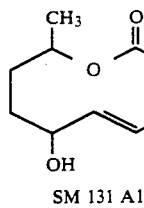 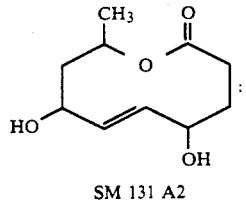

SM 131 A1                SM 131 A2

The compounds SM 131 A1 and A2 exist as a mixture of isomers (about 1:1) and have not been separated.

Thin-layer chromatography: Silica gel 60 $F_{254}$:. chloroform/methanol (9:1, v:v): Rf 0.40 n-butanol/acetic acid/water (upper phase) (4:1:5, v:v:v): Rf 0.60

EI-MS (70 eV) of the bis-trimethylsilyl ether: m/e=344 (M+, 1%): 274 (M+H-Me$_3$Si, 1%): 201 (M+H-2Me$_3$Si) corresponding to $C_{10}H_{16}O_4$ (200.24) for SM 131 A1/A2 Melting point: 100° C.

IR (KBr): 3400, 2980, 2940, 2870, 2860, 1720, 170 0 sh cm$^{-1}$

UV (MeOH): end absorption $^1$H NMR (200 MHz) CD$_3$OD): SM 131 A1 +A2
δ=1.15 (d, 3H, J=6.3 Hz, 9-CH$_3$); 1.20 (d, 3H, J=6.7 Hz, 9-CH$_3$); 1.43 (dd, 1H, J =16/7.5 Hz); 1.6-1.8 (m, 5H); 1.8-2.0 (m, 2H); 2.30 (dd, 1H, J=13.4/5.6 Hz); 2.50 (m, 2H); 2.92 (dd, 1H, J=13.4/7.7 Hz); 3.94 (m, 1H); 4.38 (m, 1H); 4 (dddd, 1H, J=7.7/6.8/5.6/1 Hz); 4.66–4.78 (m, 2H); 4.99 (dq, 1H, J=6.7/3.5 Hz); 5.40 + 5.55 (AB system, each 1 dd, 2H, J=16/8.2 and 16/6.8 Hz, olefin H); 5.77 + 5.90 (AB system, each 1 ddd, 2H, J=16/2.3/1 and 16/2.8/1.4 Hz, olefin H) ppm.

C NMR (50.3 MHz, CD$_3$OD): δ=18.9 q (9-CH$_3$); 22.1 q (9-CH$_3$); 28.6 t; 29.2 t; 32.6 t; 36.2 t; 45.3 t (C-2); 45.8 t (C-2); 68.7 d; 69.0 d; 70.3 d; 72.3 d; 74.1 d; 130.6 d; 131.9 d; 138.2 d; 172.0 s (C-1); 172.4 s (C-1) ppm.

Elemental analysis: Calculated: C 60.00, H 8.00 Found C 60.40; H 8.09.

2. characteristics of the compound SM 133

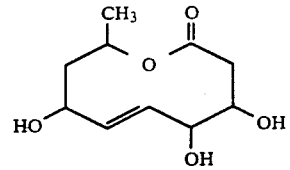

Thin-layer chromatography Silica gel 60 $F_{254}$: chloroform/methanol (9:1, v:v): Rf 0.30 n-butanol/acetic acid/water, upper phase (4:1:5): Rf 0.60

EI-MS (70 eV): no molecular ion, m/e=110 ($C_7H_{10}O$, 40%) 86 ($C_4H_6O_2$, 100%)

IR (film): 3400, 2970, 2930, 2905, 1715 sh, 1700, 1640 cm$^{-1}$

UV (MeOH): End absorption $^1$H NMR (200 MHz, CDCl$_3$): δ=1.25 (d, 3H, J=6.5 Hz, 9-CH$_3$); 1.67 (ddd, 1H, J=14/10.8/10.8 Hz, 8-H$_a$); 1.82 (ddd, 1H, J=14/3.8/2 Hz, 8-H$_b$); 2.29 (dd, 1H, J=14.2/7.2 Hz, 2-H$_a$); 2.53 (dd, 1H, J=14.2/2.8 Hz, 2-H$_b$); 3.0-3.7 (s, br, 3H, 3 OH, exchangeable); 3.95 (ddd, 1H, J=7.2/5/2.8 Hz, 3-H); 4.07 (dddd, 1H, J=10.8/7.2/3.8/2.8 Hz, 7-H); 4.13 (ddd, 1H, J=5/2/1 Hz, 4-H); 5.20 (ddq, 1H, J=10.8/6.5/2 Hz, 9-H); 5.7-5.94 (m, 2H, AB system, 5-H, 6-H) ppm.

C NMR (50.3 MHz, CD$_3$OD): δ=21.7 q (9-CH:); 35.2 t (C-8); 44.1 t (C-2); 69.3 d; 73.0 d; 73.5 d; 75.3 d; 129.4 d; 135.8 d; 174.7 s (C-1) ppm.

[α] (c=1, methanol):−62°

Elemental analysis: Calculated: C 55.55; H 7.41 (for $C_{10}H_{16}O_5$, MW 216.24) Found: C 55.73; H 7.48

3. characteristics of the compounds SM 140 $A_1/A_2$ and SM 140 B

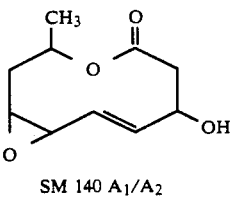 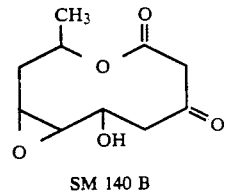

SM 140 A$_1$/A$_2$        SM 140 B

Mixture of diasteromers in the ratio $A_1/A_2$=2:1

Thin-layer chromatography: Silica gel 60 $F_{354}$, chloroform/methanol (9:1, v:v): Rf 0.60 n-butanol/acetic acid/water (upper phase) (4:1:5): Rf 0.80, Compound SM 140 A$_1$/A$_2$;

Positive fast atom bombardment MS: m/e =199 (M +H+, 84%) corresponding to $C_{10}H_{14}O_4$ (198.22)

IR (KBr): 3460, 3390, 3005, 2965, 2940, 2915, 2900, 2875, 1715, 1680 cm$^{-1}$

UV (MeOH): end absorption $^1$H NMR (200 MHz, CDCl$_3$):

Signals A1:
δ=1.45 (d, 3H, J=7 Hz, 9-CH:); 1.95 (ddd, 1H, J=15/11/10 Hz , 8- H ); 2.12 (ddd, 1H, J= 15/5/1.5 Hz, 8-H$_b$); 2.33 (dd, 1H, J=11.9/9.5 Hz, 2-H$_a$); 2.83 (dd, 1H, J=11.9/6.6 Hz, 2-H$_b$); 3.05 (ddd, 1H, J=10/5/4.2 Hz, 7-H); 3.57 (dd, 1H, J=8/4.2 Hz, 6-H); 4.65 (ddq, 1H, J=11/7/1 Hz , 9-H); 4.65 (ddd, 1H, J=9.5/8.6/6.6 Hz, 3-H); 5.42 (dd, 1H, J=16.8/8 Hz, 5-H); 5.84 (dd, 1H, J=16.8/8.6 Hz, 4-H) ppm.

Signals A2: δ=1.39 (d, 3H, J=6.8 Hz, 9-CH:); 1.83 (ddd, 1H, J=16/6.5/4.8 Hz, 8-H ); 2.22 (m, 1H, 8-H$_b$; 2.43 (dd, 1H, J=12/3 Hz, 2-H$_a$); 2.63 (dd, 1H, J =12/4.2 Hz, 2-H$_b$); 3.19 (ddd, 1H, J=6.5/5/4 Hz, 7-H); 3.50 (m, 1H, 6-H); 4.8 (m, 2H, 3-H, 9-H); 5.77 (ddd, 1H, J=15.5/2/1 Hz, 5-H); 6.07 (ddd, 1H, J=15.5/1.8/1.5 Hz, 4-H) ppm.

C NMR (50.3 MHz CDCl$_3$)

Signals A$_1$: δ=21.5 q (9-CH$_3$; 34.6 t (C-8); 45.7 t (C-2); 5.0 d; 55.2 d; 71.6 d; 71.7 d; 129.7 d; 133.9 d; 70.7 s (C-1) ppm.

Signals A$_2$: δ=19.0 q (9-CH$_3$); 29.0 t (C-8); 44.4 t (C-2); 53.5 d; 54.1 d; 68.2 d; 69.3 d; 120.1 d; 136.7 d; 171.1 s (C-1) ppm.

Compound SM 140 B

DCI-MS: m/e=249 (M + NH$_3$ + NH$_4^+$, 100%) corresponding to C$_{10}$H$_{14}$O$_5$ (214.22)

IR (KBr): 3410, 3350, 3000, 2980, 2940, 1740, 1700 cm$^{-1}$

UV (methanol): end absorption $^1$H NMR (200 MHz, CDCl$_3$): δ=1.34 (d, 3H, J=6.3 Hz, 9-CH:); 1.53 (ddd, 1H, J=14.5/10.4/11.4 Hz, 8-H$_a$); 2.36 (ddd, 1H, J=14.5/4.3/1.2 Hz, 8-H$_b$); 2.58 (d, 1H, J=2.4 Hz, exchangeable 5-OH); 2.79 (dd, 1H, J = 13.2/3.7 Hz, 4-H$_a$); 2.87 (dd, 1H, J=13.2/6 Hz, 4-H$_b$) 3.00 (dd 1H J=9/4 Hz, 6-H); 3.19 (ddd, 1H, J≦10.4/4.3/4 Hz, 7-H); 3.48 (dd, 2H, AB system, J=14.,5 Hz, 2-H$_2$); 3.83 dddd, 1H, J= 9/6/3.7/2.4 Hz, 5-H); 5.15 (ddeq, 1H, J= 11.4/6.3/1.2 Hz, 9-H) ppm.

C NMR (50.3 MHz, CDCl$_3$): δ=20.6 q (9-CH$_3$); 36.5 t (C-8); 48.4 t (C-4); 51.9 t (C-2); 56.0 d, 60.5 d; 67.7 d; 69.1 d; 165.4 s (C-1); 200.8 s (C-3) ppm.

We claim:

1. A compound of the formula I:

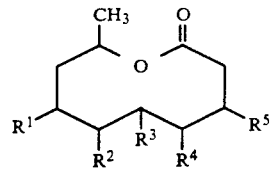

in which, independently of one another,
R$^1$ is hydrogen, hydroxyl, or together with R$^2$ and the carrying carbon atoms forms an oxirane ring;
R$^2$ is hydroxyl, or together with R$^3$ forms a double bond, or together with R$^1$ and the carrying carbon atoms forms an oxirane ring;
R$^3$ is hydroxyl, or together with R$^2$ forms a double bond, or together with R$^4$ forms a double bond;
R$^4$ is hydrogen, hydroxyl, or together with R$^3$ forms a double bond; and
R$^5$ is hydrogen, hydroxyl or an oxogroup.

2. A compound according to claim 1, wherein R$^1$ and R$^2$, together with the carrying carbon atoms, form an oxirane ring.

3. A compound according to claim 1, wherein R$^2$ and R$^3$ together form a double bond.

4. A compound according to claim 1, wherein R$^3$ and R$^4$ together form a double bond.

5. A method of treating humans or animals for bacterial infections, which comprises: administering to said human or animal an amount of the compound of formula I as claimed in claim 1 effective to treat said bacterial infection.

* * * * *